United States Patent

Baroni et al.

(10) Patent No.: US 6,689,797 B2
(45) Date of Patent: Feb. 10, 2004

(54) TETRAHYDROPYRIDINES, PREPARATION METHOD AND PHARMACEUTICAL COMPOSITIONS CONTAINING SAME

(75) Inventors: Marco Baroni, Vanzago-Milano (IT); Bernard Bourrie, Saint Gely Du Fesc (FR); Rosanna Cardamone, Como (IT); Pierre Casellas, Montpellier (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 10/169,528

(22) PCT Filed: Dec. 29, 2000

(86) PCT No.: PCT/FR00/03741

§ 371 (c)(1),
(2), (4) Date: Oct. 15, 2002

(87) PCT Pub. No.: WO01/49684

PCT Pub. Date: Jul. 12, 2001

(65) Prior Publication Data

US 2003/0083347 A1 May 1, 2003

(30) Foreign Application Priority Data

Jan. 6, 2000 (FR) .............................. 00 00113

(51) Int. Cl.⁷ .................... A61K 31/44; A61K 31/445; C07D 405/10; C07D 409/10; C07D 409/14

(52) U.S. Cl. .................... 514/333; 514/337; 546/256; 546/281.1; 546/284.1

(58) Field of Search .............. 546/256, 281.1, 546/284.1; 514/333, 337

(56) References Cited

U.S. PATENT DOCUMENTS 3,821,234 A  6/1974  Koppe et al.

FOREIGN PATENT DOCUMENTS

| DE | 2060816 | 6/1972 |
|---|---|---|
| GB | 2310376 | 8/1997 |
| WO | WO 92/07831 | 5/1992 |
| WO | WO 92/19594 | 11/1992 |
| WO | WO 99/65880 | 12/1999 |

*Primary Examiner*—Bernard Dentz
(74) *Attorney, Agent, or Firm*—Michael D. Alexander

(57) ABSTRACT

The present invention relates to compounds of formula (I):

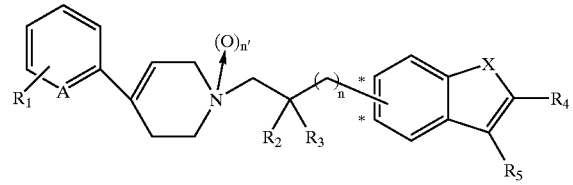

in which $R_1$ represents a hydrogen or halogen atom, or a group $CF_3$;

$R_2$ and $R_3$ represent, independently, a hydrogen atom or a methyl group;

n and n' each represent, independently, 0 or 1;

* represents the positions of attachment;

A represents N or CH;

X represents a sulfur or oxygen atom;

$R_4$ and $R_5$ represent, independently, a hydrogen atom or a ($C_1$–$C_6$) alkyl group;

and also their salts or solvates, to a method for the preparation thereof and to the pharmaceutical compositions containing them.

22 Claims, No Drawings

TETRAHYDROPYRIDINES, PREPARATION METHOD AND PHARMACEUTICAL COMPOSITIONS CONTAINING SAME

This application is a 371 of PCT/FR00/03741 filed Dec. 29, 2000.

The present invention relates to novel tetrahydropyridines, to a method for the preparation thereof and to the pharmaceutical compositions containing them.

WO92/07831 describes tetrahydropyridines substituted with a benzofuran-6-yl alkyl group carrying a triple bond in the alkyl chain, having dopaminergic activity.

It has now been found that certain tetrahydropyridines, substituted with a benzofuryl alkyl radical or benzothienyl alkyl radical, have powerful activity with respect to the modulation of TNF-alpha (from Tumour Necrosis Factor).

TNF-alpha is a cytokine which has recently provoked interest as a mediator of immunity, of inflammation, of cell proliferation, of fibrosis, etc. There is a very high concentration of this mediator in inflamed synovial tissue and it exercises an important role in the pathogenesis of autoimmunity (Annu. Rep. Med. Chem., 1997, 32:241–250).

Thus, according to one of its aspects, the present invention relates to tetrahydropyridines of formula (I):

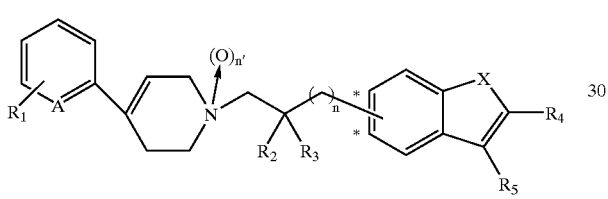

in which
$R_1$ represents a hydrogen or halogen atom, or a group $CF_3$;
$R_2$ and $R_3$ represent, independently, a hydrogen atom or a methyl group;
n and n' each represent, independently, 0 or 1;
* represents the positions of attachment;
A represents N or CH;
X represents a sulfur or oxygen atom;
$R_4$ and $R_5$ represent, independently, a hydrogen atom or a ($C_1$–$C_6$) alkyl group;
and their salts or solvates.

In the present description, the term "($C_1$–$C_6$) alkyl" denotes a monovalent radical comprising a straight- or branched-chain saturated $C_1$–$C_6$ hydrocarbon.

In the present description, the term "halogen" denotes an atom chosen from chlorine, bromine, iodine and fluorine.

Preferred compounds are those in which n is zero.

Other preferred compounds are those in which $R_1$ is in position 3 of the benzene.

Other preferred compounds are those in which $R_1$ is a group $CF_3$.

Other preferred compounds are those in which $R_2$ and $R_3$ are each a hydrogen atom.

Other preferred compounds are those in which $R_4$ and $R_5$ are each a methyl group.

The salts of the compounds of formula (I) according to the present invention comprise both the addition salts with pharmaceutically acceptable inorganic or organic acids, such as hydrochloric, hydrobromic, sulfate, hydrogen sulfate, dihydrogen phosphate, citrate, maleate, tartrate, fumarate, gluconate, methanesulfonate, 2-naphthalenesulfonate, etc., and the addition salts which allow suitable separation or crystallization of the compounds of formula (I), such as picrate, oxalate or the addition salts with these optically active acids, for example camphosulfonic acids and mandelic or substituted mandelic acids.

The stereoisomers which are optically pure, and also the mixtures of isomers of the compounds of formula (I), due to the asymmetric carbon, when one of $R_2$ and $R_3$ is a methyl and the other a hydrogen, in any proportion, are part of the present invention.

The compounds of formula (I) can be synthesized using a method which envisions
(a) reacting the compound of formula (II):

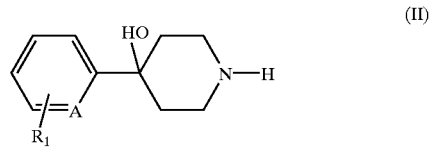

in which A and $R_1$ are defined as above, with a functional derivative of the acid of formula (III):

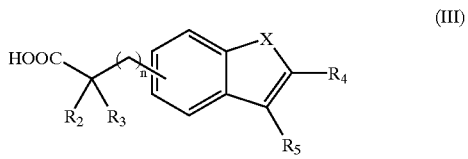

in which $R_2$, $R_3$, $R_4$, $R_5$, n and X are as defined above,
(b) reducing the carbonyl group of the compound of formula (IV):

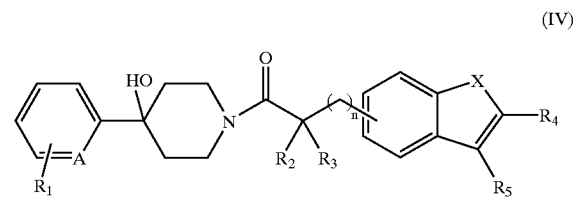

(c) dehydrating the intermediate piperidinol of formula (V):

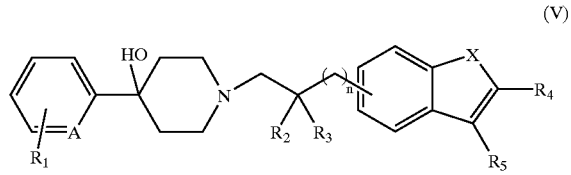

(d) isolating the compound of formula (I) thus obtained and, optionally, transforming it into one of its salts or solvates, or its N-oxide (n'=1 in formula I).

As a suitable functional derivative of the acid of formula (III), use may be made of the free acid, optionally activated (for example with BOP=benzotriazol-1-yloxytris (dimethylamino)phosphonium hexafluorophosphate), an anhydride, a mixed anhydride, an active ester or an acid halide, preferably bromide. Among the active esters, the p-nitrophenyl ester is particularly preferred, but the methoxyphenyl, trityl and benzhydryl esters and similar esters are also suitable.

The reaction of step (a) can be suitably carried out in an organic solvent at a temperature of between −10° C. and the reflux temperature of the reaction mixture.

It may be preferable to carry out the reaction under cold conditions when it is exothermic, as when chloride is used as the functional derivative of the acid of formula (III).

As the reaction solvent, use is preferably made of a halogen-based solvent, such as methylene chloride, dichloroethane, 1,1,1-trichloroethane, chloroform and the like, but also of other organic solvents compatible with the reagents used, for example dioxane, tetrahydrofuran or a hydrocarbon such as hexane, may also be used.

The reaction may be suitably carried out in the presence of a proton acceptor, for example of an alkali metal carbonate or of a tertiary amine such as triethylamine.

The reduction of step (b) can be suitably carried out with suitable reducing agents, such as borane complexes, for example borane dimethyl sulfide ($[CH_3]_2S—BH_3$), aluminum hydrides or a complex hydride of lithium and aluminum, in an inert organic solvent at a temperature of between 0° C. and the reflux temperature of the reaction mixture according to usual techniques.

The term "inert organic solvent" is intended to mean a solvent which does not interfere with the reaction. Such solvents are, for example, ethers, such as diethyl ether, tetrahydrofuran (THF), dioxane or 1,2-dimethoxyethane.

According to a preferential embodiment, the procedure is carried out with borane dimethyl sulfide used in excess relative to the starting compound (II), at the reflux temperature, optionally under inert atmosphere. The reduction is normally terminated after a few hours.

The dehydration of step (c) is easily carried out, for example, using an acetic acid/sulfuric acid mixture, at a temperature of between ambient temperature and the reflux temperature of the solvent used, or using para-toluenesulfonic acid in an organic solvent, such as, for example, benzene, toluene or chlorobenzene.

The compounds of formula (I) may also be prepared by condensation of a tetrahydropyridine of formula (VI):

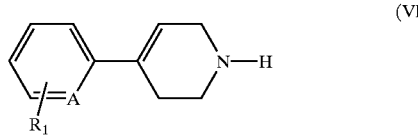

(VI)

in which A and $R_1$ are as defined above, with a compound of formula (VII):

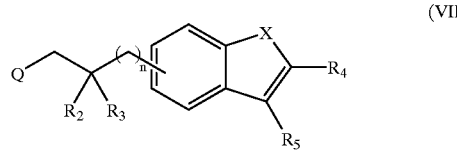

(VII)

in which $R_2$, $R_3$, $R_4$, $R_5$, n and X are as defined above and Q is a leaving group, isolation of the compound of formula (I) thus obtained and optional transformation into one of its salts or solvates, or its N-oxide.

As leaving group Q, use may be made, for example, of a halogen atom or any group which can be condensed with an amine. The condensation reaction is carried out conventionally by mixing the starting compounds (VI) and (VII) in an organic solvent such as an alcohol, for example methanol or butanol, in the presence of a base such as an alkali metal carbonate, at a temperature of between ambient temperature and the reflux temperature of the solvent chosen.

The desired compound is isolated according to conventional techniques in the form of a free base or of one of its salts. The free base may be transformed into one of its salts by simple salification in an organic solvent such as an alcohol, preferably ethanol or isopropanol, an ether such as 1,2-dimethoxyethane, ethyl acetate or acetone, or a hydrocarbon such as hexane. It may be transformed into N-oxide by oxidation according to conventional methods, for example with 3-chloroperbenzoic acid.

The starting compounds of formulae (II), (III), (VI) and (VII) are known or else they may be prepared in a similar way to the known compounds.

The compounds of the invention have properties which are advantageous with respect to the inhibition of TNF-α.

These properties were demonstrated using a test aimed at measuring the effect of molecules on TNF-α synthesis induced in Balb/c mice by lipopolysaccharide (LPS) of *Escherichia Coli* (055:B5, Sigma, St Louis, Mo.).

The products to be tested are administered orally to groups of 5 female 7- to 8-week-old Balb/c mice (Charles River, France). One hour later, the LPS is administered intravenously (10 μg/mouse). A blood sample is taken from each animal 1.5 hours after administration of the LPS. The samples are centrifuged and the plasma is recovered and frozen at −80° C. The TNF-α is measured using commercial kits (R and D, Abingdon, UK).

In this test, compounds representative of the invention proved to be very active, inhibiting TNF-α synthesis even at very low doses.

Due to this activity, and to their low toxicity, the compounds of formula (I) and its salts or solvates may indeed be used in the treatment of diseases related to immune and inflammatory disorders. In particular, the compounds of formula (I) may be used to treat atherosclerosis, autoimmune diseases, diseases which lead to the demyelinization of neurons (such as multiple sclerosis), asthma, rheumatoid arthritis, fibrotic diseases, idiopathic pulmonary fibrosis, cystic fibrosis, glumerulonephritis, rheumatoid spondylitis, osteoarthritis, gout, bone and cartilage resorption, osteoporosis, Paget's disease, multiple myeloma, uveoretinitis, septic shock, septicemia, endotoxic shock, graft-versus-host reaction, graft rejection, adult respiratory distress syndrome, silicosis, asbestosis, pulmonary sarcoidosis, Crohn's disease, ulcerative colitis, amyotrophic lateral sclerosis, Alzheimer's disease, Parkinson's disease, lupus erythematosus disseminatus, hemodynamic shock, ischemic pathological conditions (myocardial infarction, myocardial ischemia, coronary vasospasm, angina, cardiac insufficiency, heart attack), postischemic reperfusion injuries, malaria, mycobacterial infections, meningitis, leprosy, viral infections (HIV, cytomegalovirus, herpes virus), AIDS-related opportunistic infections, tuberculosis, psoriasis, atopic and contact dermatosis, diabetes, cachexia, cancer and radiation-mediated damage.

The compounds of formula (I) and their pharmaceutically acceptable salts and solvents are administered orally or parenterally, preferably orally.

In the pharmaceutical compositions of the present invention orally, the active principle may be administered in unit administration forms, as a mixture with conventional pharmaceutical carriers, to animals and humans for treating the abovementioned disorders. The suitable unit administration forms comprise, for example, tablets, optionally scored, gelatin capsules, powders, granules and oral solutions or suspensions.

When a solid composition is prepared in the form of tablets, the main active ingredient is mixed with a pharmaceutical vehicle, such as gelatin, starch, lactose, magnesium stearate, talc, gum arabic or the like. The tablets may be coated with sucrose or other suitable materials, or they may be treated such that they have prolonged or delayed activity and that they continuously release a predetermined amount of active principle.

A preparation of gelatin capsules is obtained by mixing the active ingredient with a diluent and pouring the mixture obtained into soft or hard gelatin capsules.

A preparation in the form of a syrup or elixir may contain the active ingredient together with a sweetener, preferably a calorie-free sweetener, methylparaben and propylparaben as antiseptics, and also a flavoring and a suitable colorant.

The water-dispersible powders or granules can contain the active ingredient as a mixture with dispersing or wetting agents, or suspending agents, such as polyvinylpyrrolidone, as well as with sweeteners or flavor enhancers.

The active principle can also be formulated in the form of microcapsules, optionally with one or more carriers or additives.

In the pharmaceutical compositions according to the present invention, the active principle can also be in the form of an inclusion complex in cyclodextrins, their ethers or their esters.

The amount of active principle to be administered depends, as always, on the degree of progression of the disease and also on the age and weight of the patient. Nevertheless, the unit doses generally comprise from 0.001 to 100 mg, better still from 0.01 to 50 mg, preferably from 0.1 to 20 mg, of active principle, advantageously from 0.5 to 10 mg.

According to another of its aspects, the present invention relates to a combination comprising a compound of formula (I), or one of its pharmaceutically acceptable salts or solvates, and at least one compound chosen from immunosuppressants, such as interferon beta-1b; adrenocorticotropic hormone; glucocorticoids such as prednisone or methylprednisolone; interleukin-1 inhibitors, methatrexate.

More particularly, the invention relates to a combination comprising a compound of formula (I), or one of its pharmaceutically acceptable salts or solvates, and at least one compound chosen from roquinimex (1,2-dihydro-4-hydroxy-N,1-dimethyl-2-oxo-3-quinolinecarboxanilide), myloran (product from the company Autoimmune containing bovine myelin), antegren (monoclonal human antibody from Elan/Athena Neurosciences) and recombinant interferon β-1b.

Other possible combinations are those consisting of a compound of formula (I), or one of its pharmaceutically acceptable salts or solvates, and a potassium-channel blocker such as, for example, fampridine (4-aminopyridine).

According to another of its aspects, the invention relates to a method for treating diseases related to immune and inflammatory disorders, in particular atherosclerosis, autoimmune diseases, diseases which lead to the demyelinization of neurons (such as multiple sclerosis), asthma, rheumatoid arthritis, fibrotic diseases, idiopathic pulmonary fibrosis, cystic fibrosis, glumerulonephritis, rheumatoid spondylitis, osteoarthritis, gout, bone and cartilage resorption, osteoporosis, Paget's disease, multiple myeloma, uveoretinitis, septic shock, septicemia, endotoxic shock, graft-versus-host reaction, graft rejection, adult respiratory distress syndrome, silicosis, asbestosis, pulmonary sarcoidosis, Crohn's disease, ulcerative colitis, amyotrophic lateral sclerosis, Alzheimer's disease, Parkinson's disease, lupus erythematosus disseminatus, hemodynamic shock, ischemic pathological conditions (myocardial infarction, myocardial ischemia, coronary vasospasm, angina, cardiac insufficiency, heart attack), postischemic reperfusion injuries, malaria, mycobacterial infections, meningitis, leprosy, viral infections (HIV, cytomegalovirus, herpes virus), AIDS-related opportunistic infections, tuberculosis, psoriasis, atopic and contact dermatosis, diabetes, cachexia, cancer and radiation-mediated damage, comprising the administration of a compound of formula (I), or of one of its pharmaceutically acceptable salts or solvates, alone or in combination with other active principles.

The following examples illustrate the invention.

EXAMPLE 1

5-(2-(4-(3-Trifluoromethylphenyl)-1,2,3,6-tetrahydropyrid-1-yl)ethyl)benzothiophene and its Oxalate.

1a) 5-(2-(4-Hydroxy-4-(3-trifluoromethylphenyl)piperidino)ethyl)benzothiophene

A mixture of 1.47 g (0.006 mol) of 4-hydroxy-4-(3-trifluoromethylphenyl)piperidine, 30 ml of methylene chloride, 2.25 ml (0.0162 mol) of triethylamine, 1.15 g (0.006 mol) of benzothiophene-5-acetic acid (prepared according to the method described in J. Med. Chem. 1997, 40(7):1049–72) and 2.7 g (0.006 mol) of BOP is stirred at ambient temperature for 3 hours. Ethyl acetate is added to the mixture and the mixture is washed with 1N hydrochloric acid and then with water, with a solution of $NaHCO_3$ and again with water. The organic phase is dried over sodium sulfate and filtered and the solvent is evaporated off. The crude product thus obtained, dissolved in 20 ml of anhydrous tetrahydrofuran (THF), is refluxed for 5 hours and 1.1 ml of a solution of $BH_3Me_2S$ and 15 ml of anhydrous THF are added thereto. The mixture is cooled to 0° C. and 20 ml of methanol are added thereto dropwise. The mixture is refluxed for 30 minutes, the methanol is evaporated off and the residue is taken up in a 1/1 $NH_4OH$/ethyl acetate mixture. The organic phase is dried over sodium sulfate, filtered and the solvent is evaporated off. The reaction crude is purified by chromatography on a silica gel column, eluting with ethyl acetate. 0.9 g of the title product is obtained.

1b) 5-(2-(4-(3-Trifluoromethylphenyl)-1,2,3,6-tetrahydropyrid-1-yl)ethyl)benzothiophene and its Oxalate.

0.8 g (0.0042 mol) of para-toluenesulfonic acid and 45 ml of chlorobenzene are heated and 25 ml of solvent are distilled. A Markusson apparatus is prepared in nitrogen atmosphere and 0.9 g (0.0022 mol) of the product of the previous step dissolved in 25 ml of chlorobenzene are added, after cooling, to the mixture. The mixture is refluxed for 2 hours and run into a saturated $NaHCO_3$ solution. The two phases are separated, the organic phase is dried over sodium sulfate and, after filtering, the solvent is evaporated. The title compound (base) is obtained and its oxalate salt is prepared using a solution of isopropanol saturated with oxalic acid.

M.P. (oxalate) 195–197° C.

EXAMPLE 2

5-(2-(4-(3-Trifluoromethylphenyl)-1,2,3,6-tetrahydropyrid-1-yl)ethyl)benzofuran and its Oxalate.

2a) Benzofuran-5-acetic Acid 5 g (0.033 mol) of 4-hydroxyphenylacetic acid are mixed in 30 ml of DMSO (dimethyl sulfoxide) and 5.7 ml of a 50% aqueous NaOH solution are added thereto. After 10 minutes at ambient temperature, 5.16 ml (0.033 mol) of bromoacetaldehyde dimethylacetal are added thereto and heated at 110° C. for 4 hours. The mixture is run into 1N hydrochloric acid and extracted with diethyl ether, the organic phase is dried over sodium sulfate and, after filtration, the solvent is evaporated off. 7.85 g (0.029 mol) of the product thus obtained are mixed in 50 ml of absolute ethanol and 1.5 mmol of p-toluenesulfonic acid are added thereto. The mixture is refluxed for 3 hours. The ethanol is evaporated off, the remainder is taken up with a 5% $NaHCO_3$ solution until a neutral pH is obtained, the organic phase is dried over sodium sulfate and, after filtration, the solvent is evaporated off. 6.57 g of polyphosphoric acid are refluxed with 40 ml of benzene and, after 15 minutes, 7.06 g of the product obtained above, dissolved in 4 ml of benzene are added thereto and the mixture is refluxed for one hour. The benzene is removed, and the residue is washed with water, with a saturated $NaHCO_3$ solution and with a saline solution. The title product is obtained, which is purified by flash chromatography, eluting with a 9/1 hexane/ethyl acetate mixture. 0.93 g of the title product are thus obtained.
2b) 5-(2-(4-(3-Trifluoromethylphenyl)-1,2,3,6-tetrahydropyrid-1-yl)ethyl)benzofuran and its Oxalate.

By carrying out the procedure as described in example 1a) and 1b), but using the product of step 2a) instead of the benzothiophene-5-acetic acid, the title compound is obtained.

M.P. (oxalate) 189–191° C.

EXAMPLE 3

6-(2-(4-(3-Trifluoromethylphenyl)-1,2,3,6-tetrahydropyrid-1-yl)ethyl)benzofuran and its Oxalate.
3a) Benzofuran-6-acetic Acid By carrying out the procedure as described in example 2a), but using 3-hydroxyphenylacetic acid instead of 4-hydroxyphenylacetic acid, the title compound is obtained.
3b) 6-(2-(4-(3-Trifluoromethylphenyl)-1,2,3,6-tetrahydropyrid-1-yl)ethyl)benzofuran and its Oxalate.

By carrying out the procedure as described in example 1a) and 1b), but using the product of step 3a) instead of benzothiophene-5-acetic acid, the title compound is obtained.

M.P. (oxalate) 179–181° C.

EXAMPLE 4

2,3-Dimethyl-5-(2-(4-(3-trifluoromethylphenyl)-1,2,3,6-tetrahydropyrid-1-yl)ethyl)benzofuran and its Oxalate.
4a) 2,3-Dimethylbenzofuran-5-acetic Acid 5 g of 4-hydroxyphenylacetic acid (0.033 mol) are mixed in 100 ml of absolute ethanol and 1.6 mmol of p-toluenesulfonic acid are added thereto. The mixture is refluxed for 3 hours. The ethanol is evaporated off and the remainder is taken up with ethyl ether and washed with a 5% $NaHCO_3$ solution until neutral pH is obtained, the organic phase is dried over sodium sulfate and, after filtration, the solvent is evaporated off. 6 g (0.033 mol) of the product thus obtained are refluxed in 150 ml of anhydrous acetone. 4.45 g (0.033 mol) of crotyl bromide, 9.33 g of potassium carbonate and 480 mg of sodium iodide are added thereto and the mixture is refluxed for 12 hours. The potassium carbonate is filtered, the acetone is evaporated off and the residue is taken up with ethyl ether and washed with water. The solvent is evaporated off and the product is heated at 220° C. without solvent for 30 minutes. 500 mg of the product thus obtained are dissolved in 20 ml of methylene chloride and 0.548 g of iodine and 0.124 microliters of $SnCl_4$ are added thereto. The mixture is stirred for 3 hours, run into a water/ice mixture and neutralized with a 0.5 N NaOH solution. The organic phase is washed with an aqueous 5% sodium bisulfite solution and then with water. 0.37 g of the product thus obtained are refluxed for 24 hours with 150 ml of methanol and 0.43 g of NaOH. The solvent is evaporated off, 1 N hydrochloric acid is added until acid pH is obtained and the mixture is extracted with ethyl acetate. The title product is obtained, which is purified by flash chromatography, eluting with a 7/3 ethyl acetate/hexane mixture.
4b) 2,3-Dimethyl-5-(2-(4-(3-trifluoromethylphenyl)-1,2,3,6-tetrahydropyrid-1-yl)ethyl)benzofuran and its Oxalate.

By carrying out the procedure as described in example 1a) and 1b), but using the product of step 4a) instead of benzothiophene-5-acetic acid, the title compound is obtained.

M.P. (oxalate) 206–208° C.

EXAMPLE 5

2-Methyl-5-(2-(4-(3-trifluoromethylphenyl)-1,2,3,6-tetrahydropyrid-1-yl)ethyl)benzofuran and its Oxalate.
5a) 2-Methylbenzofuran-5-acetic Acid By carrying out the procedure as described in example 4a), but using allyl bromide instead of crotyl bromide, the title compound is obtained.
5b) 2-Methyl-5-(2-(4-(3-trifluoromethylphenyl)-1,2,3,6-tetrahydropyrid-1-yl)ethyl)benzofuran and its Oxalate.

By carrying out the procedure as described in example 1a) and 1b), but using the product of step 5a), instead of benzothiophene-5-acetic acid, the title compound is obtained.

M.P. (oxalate) 161–163° C.

EXAMPLE 6

3-Methyl-5-(2-(4-(3-trifluoromethylphenyl)-1,2,3,6-tetrahydropyrid-1-yl)ethyl)benzofuran and its Oxalate.
6a) 3-Methyl(benzofuran-5-yl)acetic Acid 5 g (0.027 mol) of ethyl 4-hydroxyphenylacetate, 120 ml of acetone, 7.8 g of $K_2CO_3$, 400 mg of sodium iodide and 2.19 ml of chloroacetone are refluxed for 5 hours. The $K_2CO_3$ is filtered, the solvent is evaporated off and the residue is taken up with ethyl ether and washed with water. 3.64 g of the product obtained are mixed in 25 ml of 2,2-dimethoxypropane and 0.4 mmol of p-toluenesulfonic acid are added thereto. The mixture is refluxed for 3 hours. Ethyl acetate is added thereto, and the solution is washed with a 5% sodium bicarbonate solution and then with a saline solution. 4.2 g of polyphosphoric acid are refluxed with 24 ml of benzene and, after 15 minutes, 3.66 g of the product obtained above, dissolved in 4 ml of benzene, are added thereto and the mixture is refluxed for one hour. The benzene is removed and the remainder is washed with water with a saturated $NaHCO_3$ solution and then with a saline solution. The product is purified by flash chromatography, eluting with a 9/1 hexane/ethyl acetate mixture. The product thus obtained is mixed with a solution of 0.22 g of KOH in 5.5 ml of methanol and heated at 80° C. for 2 hours. The solvent is evaporated off and the residue is taken up in a 1 N hydrochloric acid solution and extracted with methylene chloride. The two phases are separated, the organic phase is dried over sodium sulfate and, after filtration, the solvent is evaporated off. The title compound is obtained.
6b) 3-Methyl-5-(2-(4-(3-trifluoromethylphenyl)-1,2,3,6-tetrahydropyrid-1-yl)ethyl)benzofuran and its Oxalate.

By carrying out the procedure as described in example 1a) and 1b), but using the product of step 6a) instead of benzothiophene-5-acetic acid, the title compound is obtained.

M.P. (oxalate) 197–198° C.

EXAMPLE 7

6-(2-(4-(3-Trifluoromethylphenyl)-1,2,3,6-tetrahydropyrid-1-yl)ethyl)benzothiophene and its Oxalate.

By carrying out the procedure as described in example 1a) and 1b) but using benzothiophene-6-acetic acid instead of benzothiophene-5-acetic acid, the title compound is obtained.

M.P. (oxalate) 200–201° C.

EXAMPLE 8

2-3-Dimethyl-6-(2-(4-(3-trifluoromethylphenyl)-1,2,3,6-tetrahydropyrid-1-yl)ethyl)benzofuran and its Oxalate.

By carrying out the procedure as described in example 1a) and 1b), but using 2,3-dimethylbenzofuran-5-acetic acid instead of benzothiophene-5-acetic acid, the title compound is obtained.

M.P. (oxalate) 196–198° C.

EXAMPLE 9

2,3-Dimethyl-6-(2-(4-(3-trifluoromethylphenyl)-1,2,3,6-tetrahydropyrid-1-yl)ethyl)benzothiophene and its Oxalate.

By carrying out the procedure as described in example 1a) and 1b), but using 2,3-dimethylbenzothiophene-5-acetic acid instead of benzothiophene-5-acetic acid, the title compound is obtained.

M.P. (oxalate) 194–196° C.

EXAMPLE 10

2,3-Dimethyl-5-(2-(4-(3-fluorophenyl)-1,2,3,6-tetrahydropyrid-1-yl)ethyl)benzofuran and its Oxalate.

10a) 2-(2,3-Dimethylbenzofuran-5-yl)ethyl Methanesulfonate.

A solution of 6.3 g of 2,3-dimethylbenzofuran-5-acetic acid in 125 ml of THF is added to a suspension of 3.06 g of lithium aluminum hydride in 30 ml of THF, under nitrogen. The mixture is refluxed for 4 hours and then 100 ml of water are added to the reaction mixture. The salt is filtered and the filtrate is evaporated under reduced pressure so as to obtain an oil. This is dissolved in 35 ml of methylene chloride, 3.5 ml of triethylamine are added and the mixture is cooled to 0–5° C. 1.4 ml of mesyl chloride are added and the mixture is stirred for 2 hours at ambient temperature. The mixture is washed with water and dried and the solvent is evaporated off under reduced pressure. Purification is carried out by chromatography, eluting with an 8/2 cyclohexane/ethyl acetate mixture and the title product is obtained.

10b) 2,3-Dimethyl-5-(2-(4-(3-fluorophenyl)-1,2,3,6-tetrahydropyrid-1-yl)ethyl)benzofuran and its Oxalate.

0.65 g (2.4 mmol) of product described in the previous step are dissolved in 20 ml of butanol. 0.52 g (2.4 mmol of 4-(3-fluorophenyl)-,1,2,3,6-tetrahydropyridine and 0.34 g (2.4 mmol) of potassium carbonate are added thereto and the mixture is refluxed for 5 hours. The solvent is evaporated off and the residue is washed with water. This is extracted with methylene chloride, the organic phase is dried and the solvent is evaporated off under reduced pressure. The residue is purified on a silica gel column, eluting with an 8/2 cyclohexane/ethyl acetate mixture, and the title product is obtained. The oxalate is prepared using acetone saturated with oxalic acid.

M.P. (oxalate) 203–205° C.

EXAMPLE 11

2,3-Dimethyl-6-(2-(4-(6-chloropyrid-2-yl)-1,2,3,6-tetrahydropyrid-1-yl)ethyl)benzofuran and its Oxalate.

11a) 2-(2,3-dimethylbenzofuran-6-yl)ethyl Methanesulfonate

By carrying out the procedure as described in example 10a), but using the 2,3-dimethylbenzofuran-6-acetic acid instead of 2,3-dimethylbenzofuran-5-acetic acid, the title compound is obtained.

11b) 2,3-Dimethyl-6-(2-(4-(6-chloropyrid-2-yl)-1,2,3,6-tetrahydropyrid-1-yl)ethyl)benzofuran and its Oxalate.

By carrying out the procedure as in example 10b), but using the product of the previous step instead of the product obtained in 10a) and 4-(6-chloropyrid-2-yl)-1,2,3,6-tetrahydropyridine instead of 4-(3-fluorophenyl)-1,2,3,6-tetrahydropyridine, the title compound is obtained.

M.P. (oxalate) 199–200° C.

EXAMPLE 12

2,3-Dimethyl-6-(2-(4-(3-trifluoromethylphenyl)-1,2,3,6-tetrahydropyrid-1-yl)ethyl)benzofuran N-oxide 0.086 g of 3-chloroperbenzoic acid is added to a solution of 0.2 g (0.5 mmol) of 2,3-dimethyl-6-(2-(4-(3-trifluoromethylphenyl)-1,2,3,6-tetrahydropyrid-1-yl)ethyl) benzofuran in 25 ml of methylene chloride at a temperature of 0–5° C. The mixture is allowed to stir for 2 hours at 0–5° C. and washed with a saturated aqueous sodium bicarbonate solution, and the two phases are separated. The organic phase is dried and then filtration and evaporation under reduced pressure are carried out. Purification is carried out by chromatography, eluting with a 1/1 methanol/ethyl acetate mixture, and the title product is obtained.

M.P. 83–86° C.

What is claimed is:

1. A compound of formula (I):

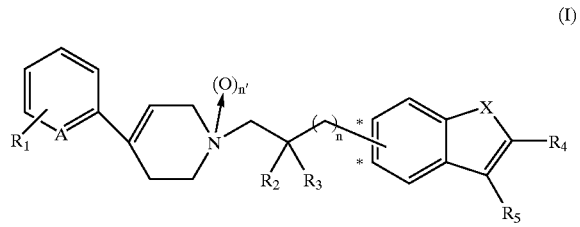

(I)

in which

R$_1$ represents a hydrogen or halogen atom, or a group CF$_3$;

R$_2$ and R$_3$ represent, independently, a hydrogen atom or a methyl group;

n and n' each represent, independently, 0 or 1;

* represents the positions of attachment;

A represents N or CH;

X represents a sulfur or oxygen atom;

R$_4$ and R$_5$ represent, independently, a hydrogen atom or a (C$_1$–C$_6$) alkyl group;

and their salts or solvates.

2. The compound as claimed in claim 1, in which n is zero.

3. The compound as claimed in claim 1, in which R$_1$ is in position 3 of the benzene.

4. The compound as claimed in claim 1, in which R$_2$ and R$_3$ are each a hydrogen atom.

5. The compound as claimed in claim 1, in which R$_1$ is a group CF$_3$.

6. The compound as claimed in claim 1, in which R$_4$ and R$_5$ are each a methyl group.

7. A method for preparing a compound of claim 1 wherein (a) the compound of formula (II):

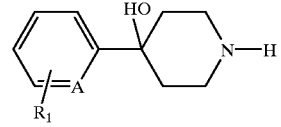

in which A and R$_1$ are defined as in claim 1, is reacted with a functional derivative of the acid of formula (III):

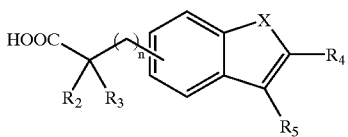

in which $R_2$, $R_3$, $R_4$, $R_5$, n and X are as defined in claim 1, (b) the carbonyl group of the compound of formula (IV):

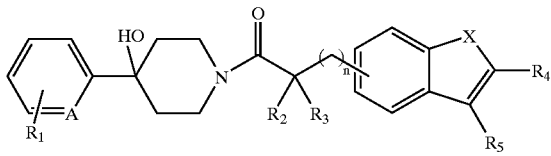

is reduced, (c) the intermediate piperidinol of formula (V):

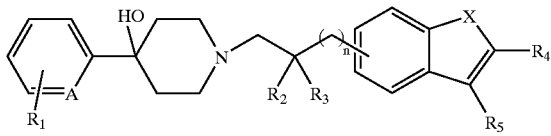

is dehydrated, (d) the compound of formula (I) thus obtained is isolated and, optionally, it is transformed into one of its salts or solvates, or its N-oxide.

8. A method for preparing a compound of claim 1 wherein a tetrahydropyridine of formula (VI):

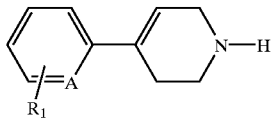

in which A and $R_1$ are as defined in claim 1, is condensed with a compound of formula (VII):

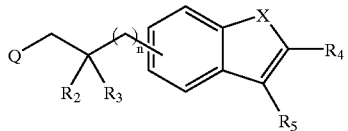

in which $R_2$, $R_3$, $R_4$, $R_5$, n and X are as defined above and Q is a leaving group, the compound of formula (I) thus obtained is isolated and is optionally transformed into one of its salts or solvates, or into its N-oxide.

9. A pharmaceutical composition containing, as active principle, a compound of formula (I) as claimed in claim 1, or one of its pharmaceutically acceptable salts or solvates.

10. The composition as claimed in claim 9 wherein it contains from 0.01 to 50 mg of active principle.

11. A pharmaceutical composition containing, as active principle, a compound of formula (I) as claimed in claim 2, or one of its pharmaceutically acceptable salts or solvates.

12. A pharmaceutical composition containing, as active principle, a compound of formula (I) as claimed in claim 3, or one of its pharmaceutically acceptable salts or solvates.

13. A pharmaceutical composition containing, as active principle, a compound of formula (I) as claimed in claim 4, or one of its pharmaceutically acceptable salts or solvates.

14. A pharmaceutical composition containing, as active principle, a compound of formula (I) as claimed in claim 5, or one of its pharmaceutically acceptable salts or solvates.

15. A pharmaceutical composition containing, as active principle, a compound of formula (I) as claimed in claim 6, or one of its pharmaceutically acceptable salts or solvates.

16. A method for the treatment of diseases related to immune and inflammatory disorders which comprises administering to a patient in need of such treatment an effective amount of a compound according to claim 1.

17. A method for the treatment of diseases related to immune and inflammatory disorders which comprises administering to a patient in need of such treatment an effective amount of a compound according to claim 2.

18. A method for the treatment of diseases related to immune and inflammatory disorders which comprises administering to a patient in need of such treatment an effective amount of a compound according to claim 3.

19. A method for the treatment of diseases related to immune and inflammatory disorders which comprises administering to a patient in need of such treatment an effective amount of a compound according to claim 4.

20. A method for the treatment of diseases related to immune and inflammatory disorders which comprises administering to a patient in need of such treatment an effective amount of a compound according to claim 5.

21. A method for the treatment of diseases related to immune and inflammatory disorders which comprises administering to a patient in need of such treatment an effective amount of a compound according to claim 6.

22. A method according to claim 16 for the treatment of atherosclerosis, autoimmune diseases, diseases which lead to the demyelinization of neurons, asthma, rheumatoid arthritis, fibrotic diseases, idiopathic pulmonary fibrosis, cystic fibrosis, glumerulonephritis, rheumatoid spondylitis, osteoarthritis, gout, bone and cartilage resorption, osteoporosis, Paget's disease, multiple myeloma, uveoretinitis, septic shock, septicemia, endotoxic shock, graft-versus-host reaction, graft rejection, adult respiratory distress syndrome, silicosis, asbestosis, pulmonary sarcoidosis, Crohn's disease, ulcerative colitis, amyotrophic lateral sclerosis, Alzheimer's disease, Parkinson's disease, lupus erythematosus disseminatus, hemodynamic shock, ischemic pathological conditions, postischemic reperfusion injuries, malaria, mycobacterial infections, meningitis, leprosy, viral infections, AIDS-related opportunistic infections, tuberculosis, psoriasis, atopic and contact dermatosis, diabetes, cachexia, cancer and radiation-mediated damage.

\* \* \* \* \*